United States Patent [19]

Kelley et al.

[11] 4,247,722

[45] Jan. 27, 1981

[54] HYDROGENATION OF BUTADIENEPOLYPEROXIDE WITH ACTIVATED PHASE-PURE NiAl$_3$ CATALYST

[75] Inventors: Michael J. Kelley, Kennett Square, Pa.; William W. Prichard, Hockessin, Del.

[73] Assignee: E. I. Du Pont de Nemours and Company, Wilmington, Del.

[21] Appl. No.: 127,456

[22] Filed: Mar. 5, 1980

Related U.S. Application Data

[63] Continuation-in-part of Ser. No. 33,438, Apr. 26, 1979, abandoned.

[51] Int. Cl.$^3$ .............................................. C07C 31/20
[52] U.S. Cl. ................... 568/861; 252/466 J; 252/477 Q
[58] Field of Search ........................................ 568/861

[56] References Cited

U.S. PATENT DOCUMENTS

| | | | |
|---|---|---|---|
| 1,628,190 | 5/1927 | Raney | 252/477 Q |
| 2,825,108 | 3/1958 | Pond | 428/606 |
| 3,627,790 | 12/1971 | Stiles | 568/861 |
| 3,896,051 | 7/1975 | Mabuchi et al. | 252/477 Q |
| 3,896,203 | 7/1975 | Maringer et al. | 264/8 |
| 4,002,692 | 1/1977 | Mabuchi et al. | 568/861 |
| 4,043,946 | 8/1977 | Sanker et al. | 252/466 J |
| 4,049,580 | 9/1977 | Oden et al. | 252/466 J |
| 4,089,812 | 5/1978 | O'Hare et al. | 252/466 J |
| 4,112,004 | 9/1978 | Mabuchi et al. | 568/861 |
| 4,123,616 | 10/1978 | Mabuchi et al. | 568/861 |

*Primary Examiner*—Joseph E. Evans

[57] ABSTRACT

A process for hydrogenation of butadienepolyperoxide to 1,2-butanediol and 1,4-butanediol which comprises hydrogenating a mixture of butadienepolyperoxide in a solvent and with a catalyst comprising an activated phase-pure NiAl$_3$ at a temperature of from 75°–120° C. and a pressure of at least 1000 psi.

8 Claims, No Drawings

HYDROGENATION OF BUTADIENEPOLYPEROXIDE WITH ACTIVATED PHASE-PURE NIAL₃ CATALYST

CROSS-REFERENCE TO RELATED APPLICATION

This application is a continuation-in-part of copending U.S. application Ser. No. 033,438 filed Apr. 26, 1979, and now abandoned.

DESCRIPTION

1. Technical Field

This invention relates to the hydrogenation of butadienepolyperoxide to saturated diols. More specifically, this invention relates to the hydrogenation of butadienepolyperoxide to 1,2-butanediol and 1,4-butanediol employing an activated phase-pure $NiAl_3$ catalyst.

2. Background Art

The use of nickel catalysts of the alloy-skeleton or Raney type in the hydrogenation of organic compounds has long been known.

Raney type nickel catalysts, however, have been found to have very short effectiveness as hydrogenation catalysts for organopolymeric peroxides, such as butadienepolyperoxide, and readily become poisoned when utilized in hydrogenation reactions with these materials. As a result, the amount of the organo-polymeric peroxide which is hydrogenated is limited and depends upon the amount of the catalysts used. Thus to increase the yield of diol per amount of the catalyst, the catalyst must be reactivated by a special treatment. U.S. Pat. No. 3,627,790 discloses that by utilizing a Ni-Al alloy containing 65-80% $NiAl_3$ it was possible to obtain a Raney type nickel catalyst which, in hydrogenation reactions, increased the rate of reaction and permitted initiation of hydrogenation reactions at lower temperatures. The patent further discloses a longer useful catalyst life by removing only portions of the aluminum during the alkali activation step thus enabling the catalyst to undergo an increased number of activations and to permit reactivation in situ. No increase in the longevity of the catalyst prior to initial reactivation or efficacy in hydrogenation reactions involving organopolyperoxides is alluded to.

The hydrogenation of butadienepolyperoxide to butanediols in the prior art gives poor yields of the desired 1,4-butanediol and includes the commercially unattractive 1,2-butanediol. The reduction is carried out using a catalyst which rapidly becomes inactivated by contact with the peroxide and must be regenerated frequently. The reduction is very exothermic and is usually done stepwise under successively more severe conditions until reduction is complete.

The catalysts of the present invention provide a solution to the problems heretofore preventing effective hydrogenation of organopolymeric peroxides. These materials have been found to be surprisingly resistant to the oxidizing effects of the peroxide material, and to possess a greatly increased catalyst life.

The preparation of 1,4-butanediol is important not only for uses as solvents and monomers for the preparation of polyesters but also for use in the preparation of tetrahydrofuran.

DISCLOSURE OF THE INVENTION

The present invention discloses a process for hydrogenation of butadienepolyperoxide to 1,2-butanediol and 1,4-butanediol. The process of this invention comprises hydrogenating a dilute solution mixture of butadienepolyperoxide in an inert solvent in the presence of hydrogen and an effective amount of catalyst comprising an alkali activated phase-pure $NiAl_3$ compound.

More specifically, the present invention discloses a process for hydrogenation of butadienepolyperoxide to 1,2-butanediol and 1,4-butanediol which comprises hydrogenating 1 to 20% by weight of butadienepolyperoxide at a temperature of from 75°–120° C. and a pressure of at least 1000 psi in the presence of a catalyst comprising an alkali activated 42% nickel-58% aluminum alloy wherein at least 98% by weight of the nickel in the alloy is present as $NiAl_3$ and in a solvent which is inert under the process conditions employed.

Butadienepolyperoxide can be prepared by converting butadiene thereto by any suitable oxidation process wherein a substantial portion of the butadiene is converted to the polyperoxide. Butadiene may be oxidized in a suitable solvent in the liquid phase in the presence of air or oxygen to form butadienepolyperoxide. The oxidation can be conducted in any suitable pressure reactor provided with means to thoroughly mix air or oxygen and the butadiene. Contact times for the oxidation are generally from 0.1–25, preferably 1–5 hours. The oxidation is conducted in the temperature range of 35°–120° C. and at a partial pressure of oxygen of at least 20 psi. An initiator is preferably used to start the oxidation. Suitable initiators are organic peroxides or other precursors of free radicals such as azobisisobutyronitrile. Oxidation promoters such as acetaldehyde, cobalt linoleate and the like may be used.

The solvent for hydrogenating the butadienepolyperoxide is any solvent for butadienepolyperoxide that under the reaction conditions of hydrogenation disclosed herein is not hydrogenated and which does not cause decomposition of the polyperoxide. Representative examples include tetrahydrofuran, ethyl acetate, methyl acetate, 50–50 toluene-tetrahydrofuran, 50–50 benzene-tetrahydrofuran, similar esters and ethers and their combinations in the hydrocarbons. For economic reasons, the most suitable solvents are those which may also be used for the preparation of the polyperoxide. Most preferred is methyl acetate.

The concentration of butadienepolyperoxide in the solvent is a minor amount for reasons of safety. Concentrations of 1–20% by weight are generally used. Preferably the concentration of butadienepolyperoxide is 2.5–10% by weight in the solvent. Concentrations lower than 1% by weight, while operable, are uneconomic while concentrations higher than 20% may be dangerous. The hydrogenation is very exothermic and, if reaction temperatures are allowed to rise above about 120° C., the polymer may decompose violently.

The catalyst of the present invention is an alkali activated 42% nickel-58% aluminum alloy wherein 98–100% by weight of the nickel in the alloy is present as $NiAl_3$. More specifically, the catalyst comprises a nickel-containing foraminous material formed by the alkali leaching of from 10 to 100% of the aluminum from an alloy of nickel and aluminum wherein at least 98% by weight of the nickel in the alloy is present as intermetallic $NiAl_3$ compound.

The alloys utilized in this invention can be prepared by a pendant-drop melt extraction such as is described in U.S. Pat. No. 3,896,203 wherein a molten drop of composition $NiAl_3$ is touched by a rotating chilled member and rapidly solidifies as it draws out to a fiber. The rapid quenching of the melt prevents disproportionation of the $NiAl_3$ to aluminum and other nickel aluminum alloys, especially $Ni_2Al_3$ (sparing alkali soluble) which would occur on slow cooling. They can also be prepared by melt-spinning $NiAl_3$ on a cooled roll, a technique used commercially for the preparation of steel reinforcing wires for concrete and described in U.S. Pat. No. 2,825,108. They can also be made by preparing $NiAl_3$ surface layer on a nickel or nickel aluminum alloy particle.

After formation, the fibers are ground to the required particle size for activation by alkali leaching. The particle size is determined by one skilled in the art for the reactor used. The leaching may be accomplished by contacting the alloy with a 1–10% sodium or potassium hydroxide solution, washing with deoxygenated water until alkali free then washing with a suitable organic solvent. Examples of solvents are methanol, methyl acetate and dioxane. The Raney type nickel material is ready for introduction into the reactor.

To obtain optimum yields of diols in the reduction of butadienepolyperoxide, it is preferable to employ a high ratio of catalyst to peroxide. If this is not done, thermal degradation of the peroxide competes with the hydrogenation and the yield of diols drops. A high catalyst ratio is achieved by injecting a polyperoxide solution into a well-stirred slurry of catalyst or through a fixed-bed catalyst at reaction conditions.

Butadienepolyperoxide hydrogenation temperatures from 75°–120° C. are generally used, with a preference for temperatures between 90°–120° C. Temperatures below 75° C., while operable, are uneconomical due to the slow reaction. Temperatures above 120° C. result in substantially more decomposition products thereby reducing the yield of diols.

The pressure may generally range rather broadly. Best yields of diols are obtained at hydrogen pressures above 1000 psi. Pressures between 1000–5000 psi $H_2$ are preferred with hydrogenation rates increasing with increasing pressure. Higher pressure may be employed but would probably not be economically desirable.

The use of continuous flow equipment for the reaction is preferred and the rate of butadienepolyperoxide injection is a function of the peroxide concentration, of the weight of catalyst in the reactor, of the reaction temperature and the hydrogen pressure. At the higher permissible temperatures and pressures, the residence time in the reactor may be a few minutes while at the lower operable temperatures, a residence time of several hours may be necessary. At 110° C. and 2300 psi $H_2$, a residence time of 30 minutes gave substantially complete hydrogenation.

EXAMPLES

The following examples will serve to illustrate the specific embodiments of the invention. All percentages in the examples are by weight unless otherwise indicated.

EXAMPLE 1—COMPARATIVE

A "Hastelloy-C" pressure vessel of 4 ml volume was packed with 2.1 g of catalyst prepared by alkali extraction of commercially available Ni-Al alloy containing 35–45% $NiAl_3$. A 5% solution of 1.15 g (0.13 eq.) of butadienepolyperoxide, 0.556 g (0.0047 eq.) of 1,6-hexanediol, as a standard for gas chromatographic analysis, in 17.7 g of dioxane was prepared. This was injected into the reactor, allowed to trickle down through the catalyst bed at 100° C. and 1000 psi $H_2$ pressure and withdrawn in 5 ml aliquots from the bottom of the reactor. Each aliquot was assayed by gas chromatography using a 10′×⅛″ "Carbowax 20-M" on "Supelcoport" at 185° with a He flow of 50 ml/min. The areas of the peaks corresponding to the two principal products, 1,2- and 1,4-butanediol, are compared to the area of the 1,6-hexanediol peak:

| Aliquot No. | Reactor Temp. °C. | Injection Rate, ml/hr | Ratio of Product/ 1,6-Hexanediol | |
|---|---|---|---|---|
| | | | 1,2-Butanediol | 1,4-Butanediol |
| 1 | 100 | 10 | 0.23 | 1.11 |
| 2 | 100 | 10 | 0.17 | 0.56 |
| 3 | 100 | 10 | 0.10 | 0.29 |
| 4 | 100 | 5 | 0.05 | 0.30 |
| 5 | 125 | 5 | 0.08 | 0.57 |

The yield of the diols decreased rapidly as the catalyst became inactivated. The catalyst bed could be reactivated by heating to 270° C. for 17 hours.

EXAMPLE 2—BEST MODE

The reactor of Example 1 was packed with 2.1 g of a catalyst prepared by alkali leaching an alloy having the composition $NiAl_3$, which had been prepared by rapid cooling of a melt of this composition and which contained no detectable Ni-Al phases other than $NiAl_3$. A solution containing 1.81 g (0.0211 eq.) of butadienepolyperoxide and 2.01 g (0.009 eq.) tetraethyleneglycol dimethylether as a reference standard in 36 g of dioxane was prepared and injected into the reactor at 100° C. and 1000 psi $H_2$ pressure. After 10 ml had been injected, an assay as in Example 1 showed the production of 1,2-butanediol in 25% yield and 1,4-butanediol in 49% yield. After 30 ml of solution had been injected, the last 5 ml at 125° C. under 2000 psi $H_2$ pressure, the yield of 1,2-butanediol was 12.9% and of 1,4-butanediol was 47.3%. This catalyst charge was used for eight days, injecting various samples of butadienepolyperoxide. On the eighth day of use, after 14 g of polymer had been passed through the reactor, a yield of 44.7% of 1,4-butanediol and 16.2% of 1,2-butanediol was obtained from the polymer samples injected at that time, or essentially equivalent activity to that of the freshly charged catalyst. The reactor was held at 100° C. under hydrogen pressure in the intervals between polymer injections. It was not necessary to regenerate the catalyst activity by heating under $H_2$ to temperatures above 200° C. The catalyst charge was used for five more days of peroxide reduction before a slight decrease in activity was noted.

EXAMPLE 3

The reactor of Example 1 was charged with a catalyst prepared by alkali leaching of a sample of alloy determined, from x-ray diffraction measurements, to be 98% pure $NiAl_3$. A 10% solution of butadienepolyperoxide in dioxane, which contained 5% of 1,6-hexanediol as a reference standard, was injected at 100° C. and 2000 psi $H_2$ pressure at 3 ml/hr. The total diol yield over a three-hour period was 68%. This catalyst charge was used for seven days with various batches of polyperoxide. On the seventh use, the average diol yield was 56%.

EXAMPLE 4

A 300-ml stainless steel autoclave, fitted with a stirrer rotating at 750 rpm having a hollow shaft through which hydrogen was introduced and dispersed under the liquid surface, was charged with 20 g of an alloy-skeleton catalyst prepared from NiAl$_3$ as described in Example 2 and 55 g of tetrahydrofuran. The reactor was heated to 110° C. and pressured to 2300 psi with H$_2$. A 10% solution of butadienepolyperoxide in tetrahydrofuran, containing 3.02% of 1,6-hexanediol as a reference standard, was injected at 70–96 ml/hr with removal of product every 30 min. When injection was complete, the autoclave was washed with 50 ml of tetrahydrofuran and the composited effluent analyzed. In the third such run, a yield of 47.4% of 1,4-butanediol, 19.6% of 1,2-butanediol, 4.2% of 2-buten-1,4-diol and 2.8% of 1-butene-3,4-diol was obtained. The same catalyst charge was used for seven such reductions in which 70 g of polyperoxide was reduced without substantial deterioration of catalyst activity.

EXAMPLE 5—CATALYST

Preparation of the rapidly quenched Al$_3$Ni fiber is as follows:

MASTER ALLOY PREPARATION

Prior to the chill-block melt-spinning runs, about 19 pounds (8.6 kilograms) of "Al$_3$Ni" (inter-metallic Al$_3$Ni compound consists of 57.959 percent aluminum and 42.041 percent nickel by weight) master alloy was prepared by melting commercial purity aluminum and nickel in the appropriate weight proportions. The two metals were induction melted in a magnesia-stabilized zirconia crucible under ⅔ atmosphere of argon.

The molten alloy was heated to about 1750° C. and held at that temperature for about 15 minutes to obtain chemical homogeneity. The alloy was then cooled in the crucible to 1200° C. and cast into copper molds to yield three 5.1 centimeter diameter bars, each approximately 25 cm long. The composition of the prepared master alloy, as determined by chemical analysis, was as follows.

| Composition of "Al$_3$Ni" Master Alloy | | | | | | | |
|---|---|---|---|---|---|---|---|
| Ni | Cu | Mg | Si | Ti | Zr | Co | Ca |
| 41.98 | 0.002 | 0.002 | 0.02 | 0.001 | 0.1 | 0.007 | 0.002 |
| 42.02 | | | | | | | |
| 42.02 | | | | | | | |
| Average 42.00 | | | | | | | |

The average nickel content was based on three independent wet chemistry determinations. Contents of the other elements were determined by optical emission spectroscopy. The 0.1 percent zirconium was attributed to melting in the zirconia crucible. While the chemical analyses indicated the master alloy was about 0.04 weight percent low in nickel, the alloy was judged appropriate for the preparation of the rapidly quenched Al$_3$Ni fibers. Ribbon fiber samples made from the master alloy submitted for X-ray analysis indicated the alloy was slightly nickel-rich relative to the Al$_3$Ni composition. 0.5 Weight percent aluminum was charged with the master alloy in each of the fiber casting runs to obtain the Al$_3$Ni composition or a slightly aluminum-rich alloy near the Al$_3$Ni compound.

The master alloy ingots were crushed using a mechanical jaw crusher to obtain pieces about 0.6 to 1.3 cm on a side, which could be charged into the melt-spinning crucibles.

FIBER PREPARATION (CHILL-BLOCK MELT-SPINNING)

In all of the fiber casting runs 150 to 200 grams of master alloy are melted in 3.2 cm O.D., 2.5 cm I.D., 38 cm long alumina (Al$_2$O$_3$) tubes. (McDaniel 99.8 percent High Purity Alumina Tubes, McDaniel Refractory Procelain Co., 510 Ninth Avenue, Beaver Falls, Pa. 15010.) Each tube contained a 20 mil (508 micron) diameter orifice. The alumina tube was contained in a graphite susceptor which was heated via a 9-turn copper coil and a 15-kw induction generator system. The susceptor was heated at a rate of about 33.3° C. per minute. After the susceptor reached about 1200° C. the molten alloy was ejected through the orifice by applying pressure (about 15 cm Hg) with argon gas. The jet with an estimated velocity of 540 centimeters per second, was directed onto a rotating, water-cooled, 20.3-cm diameter copper drum. The drum rotational speed was 2500 RPM, for an equivalent surface velocity of 26.6 meters per second. The copper wheel was polished with 600 grit paper or Linde A compound prior to each run.

The entire fiber casting system was contained in a closed chamber. As part of each run, the chamber was evacuated to $5 \times 10^{-4}$ cm Hg and backfilled with argon prior to melting the charge. The 590 grams of sample fiber were cast in one atmosphere of argon. The ribbon fibers were ground to a powder. The powder material was activated by leaching with 10 ml of 10% NaOH in 30 ml of H$_2$O, washed with deoxygenated H$_2$O until alkali-free and finally washed with a solvent.

The foregoing examples illustrate the scope of the invention and the intrinsic superiority of utilizing activated phase pure NiAl$_3$ catalysts for the hydrogenation of butadienepolyperoxide to 1,2- and 1,4-butanediol.

We claim:

1. A process for hydrogenation of butadienepolyperoxide to 1,2-butanediol and 1,4-butanediol which comprises hydrogenating 1 to 20% by weight of butadienepolyperoxide at a temperature of from 75°–120° C. and a pressure of at least 1000 psi in the presence of a catalyst comprising an alkali activated 42% nickel-58% aluminum alloy wherein at least 98% by weight of the nickel in the alloy is present as NiAl$_3$ and in a solvent which is inert under the process conditions employed.

2. The process of claim 1 wherein the catalyst comprises a nickel-containing foraminous material formed by the alkali leaching of from 10 to 100% of the aluminum from an alloy consisting of nickel and aluminum wherein at least 98% by weight of the nickel in the alloy is present as intermetallic NiAl$_3$ compound.

3. The process of claim 2 wherein essentially 100% by weight of the nickel in the alloy is present as intermetallic NiAl$_3$ compound.

4. The process of claim 1 wherein the temperature is from 90°–120° C.

5. The process of claim 1 wherein the pressure is from 1000 to 5000 psi.

6. The process of claim 1 wherein 2.5% by weight butadienepolyperoxide is hydrogenated.

7. Process of claim 1 wherein the solvent is methyl acetate, tetrahydrofuran, 50% by weight toluene-50% by weight tetrahydrofuran or 50% by weight benzene-50% by weight tetrahydrofuran.

8. The process of claim 6 wherein the solvent is methyl acetate.

* * * * *